United States Patent [19]
Ares et al.

[11] Patent Number: 5,399,584
[45] Date of Patent: Mar. 21, 1995

[54] USE OF FLAVONE DERIVATIVES FOR GASTROPROTECTION

[75] Inventors: Jeffrey J. Ares, Hamilton, Ohio; Sunil V. Kakodkar, Bethlehem, Pa.; Gary R. Kelm, Cincinnati; Peter D. Murray, Fairfield, both of Ohio; Jared L. Randall, Plymouth, N.Y.; Candice L. Slough, Middletown, Ohio

[73] Assignee: The Procter & Gamble Company, Cincinnati, Ohio

[21] Appl. No.: 15,771

[22] Filed: Feb. 10, 1993

Related U.S. Application Data

[63] Continuation-in-part of Ser. No. 878,582, May 5, 1992, abandoned.

[51] Int. Cl.$^6$ .................... A61K 31/38; A61K 31/35; A61K 31/19; A61K 31/40; A61K 49/00
[52] U.S. Cl. ...................... 514/432; 514/413; 514/456; 514/570; 514/922; 514/925; 514/926; 514/927; 424/10
[58] Field of Search ............... 514/432, 456, 925, 926, 514/927, 434, 570, 413, 922; 424/10

[56] References Cited

U.S. PATENT DOCUMENTS

| | | | |
|---|---|---|---|
| 3,155,579 | 11/1964 | Perrault | 167/65 |
| 3,495,009 | 2/1970 | Tronche | 514/456 |
| 4,707,360 | 11/1987 | Brasey | 514/456 |
| 4,891,356 | 1/1990 | Szabo | 514/2 |
| 5,106,871 | 4/1992 | Komazawa et al. | 514/571 |

FOREIGN PATENT DOCUMENTS

| | | |
|---|---|---|
| 888982 | 9/1981 | Belgium . |
| 0244832 | 11/1987 | European Pat. Off. . |
| 47-44609 | 11/1972 | Japan . |
| 48-42448 | 4/1973 | Japan . |
| 48-99312 | 12/1973 | Japan . |
| 48-99313 | 12/1973 | Japan . |
| 51-23268 | 2/1976 | Japan . |
| 55-27112 | 2/1980 | Japan . |
| 55-143913 | 11/1980 | Japan . |
| 3-5424 | 1/1991 | Japan . |
| 75308 | 2/1982 | Romania . |
| 90578 | 11/1986 | Romania . |
| 555888 | 5/1977 | U.S.S.R. . |

OTHER PUBLICATIONS

Remington's Pharmaceutical Sciences, 16th edition, (1980) p. 431.
Alcaraz, M. J. & J. R. S. Hoult, "Actions of Flavonoids and the Novel Anti-Inflammatory Flavone, Hypolaetin-8-Glucoside, on Prostaglandin Biosynthesis and Glucoside, on Prostaglandin Biosynthesis and Inactiva- (List continued on next page.)

*Primary Examiner*—Raymond J. Henley, III
*Attorney, Agent, or Firm*—David L. Suter; Jacobus C. Rasser; Milton B. Graff, IV

[57] ABSTRACT

The subject invention relates to methods for preventing or treating damage to the mucosal lining of the gastrointestinal tract of a human or lower animal by administering a safe and effective amount of a compound having the structure:

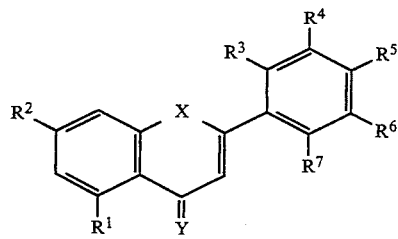

wherein X and Y are each independently selected from O and S; $R^1$, $R^2$ and $R^3$ are each independently selected from hydrogen, hydroxy, halo, unsubstituted or monosubstituted straight or branched $C_1$-$C_4$ alkanyl, and unsubstituted or substituted straight or branched $C_1$-$C_4$ alkanoxy; and each of $R^4$, $R^5$, $R^6$ and $R^7$ is hydrogen or, if one or more of $R^1$, $R^2$ and $R^3$ is other than hydrogen, each of $R^4$, $R^5$, $R^6$ and $R^7$ is selected from hydrogen, halo, trifluoromethyl, and unsubstituted straight or branched $C_1$-$C_4$ alkanyl.

19 Claims, No Drawings

OTHER PUBLICATIONS tion", Biochemical Pharmacology, vol. 34, No. 14 (1985), pp. 2477–2482.

Arakawa, T., A. Nakamura, H. Yamada, H. Nebiki, H. Satoh, T. Fukoda & K. Kobayashi, "Protection of Gastric Surface Epithelial Cells of Rats by 16,16-Dimethyl Prostaglandin $E_2$ and Sofalcone, a Synthetic Flavonoid Derivative of Sophoradin, against Ethanol", Digestion, vol. 41 (1988), pp. 61–67.

Barnaulov, O. D., O. A. Manicheva, G. G. Zapesochnaya, V. L. Shelyuto & V. I. Glyzin, "Effect of Some Flavonoids on the Ulcerogenic Activity of Reserpine in Mice", Khim.-Farm. Zh., vol. 16, No. 3 (1982), pp. 300–303.

Barnaulov, O. D., O. A. Manicheva & P. P. Denisenko, "A Method for Evaluating the Effect of Drugs on the Ulcerogenic Activity of Reserpine in Mice", Farmakol. Toksikol. (Moscow), vol. 45, No. 4 (1982), pp. 105–110.

Barnaulov, O. D., O. A. Manicheva & N. F. Komissarenko, "Comparative Evaluation of the Effect of Some Flavonoids on Changes in the Gastric Wall of Reserpine-Treated or Immobilized Mice", Khim.-Khim. Zh., vol. 17, No. 8 (1983), pp. 946–951.

Barnaulov, O. D., O'A. Manicheva, V. L. Shelyuto, M. M. Konopleva & V. I. Glyzin, "Effect of Flavonoids on the Development of Experimental Stomach Dystrophy in Mice", Khim.-Far. Zh., vol. 18, No. 8 (1984), pp. 935–941.

Barnaulov, O. D., O. A. Manicheva, I. I. Chemesova & N. F. Komissarenko, "Comparative Evaluation of the Effect of Flavonoids on the Development of Experimental Lesions of the Mouse Stomach", Khim.-Farm. Zh., vol. 18, No. 11 (1984), pp. 1330–1333.

Barnaulov, O. D., O. A. Manicheva, R. K. Yakovlev, "Evaluation of the Effects of Flavonoids from the Aerial Parts of Astragalus Quisqualis Bunge and A. Floccosifolius Sumn. on the Development of Experiemntal Lesions in the Mouse Stomach", Rastit. Resur., vol. 21, No. 1 (1985), pp. 85–90.

Boughton-Smith, N. K. & B. J. R. Whittle, "Failure of the Inhibition of Rat Gastric Mucosal 5-Lipoxygenase by Novel Acetohydroxamic Acids to Prevent Ethanol-induced Damage", British Journal of Pharmacology, vol. 95 (1988), pp. 155–162.

Brasseur, T., "Proprietes Anti-inflammatoires de Flavonoides", J. Pharm. Belg., vol. 44, No. 3 (1989), pp. 235–241.

Ciaceri, G. & G. Attaguile, "Effects of Luteolin, Apigenin, and Acacetin on Experimentally Induced Gastric Ulcer", Minerva Med., vol. 63, No. 29 (1972), pp. 1665–1668.

Corvazier, E. & J. Maclouf, "Interference of Some Flavonoids and Non-Steroidal Anti-Inflammatory Drugs with Oxidative Metabolism of Arachidonic Acid by Human Platelets and Neutrophils", Biochimica et Biophysica Acta, vol. 835 (1985), pp. 315–321.

Cristoni, A., S. Malandrino & M. J. Magistretti, "Effect of a Natural Flavonoid on Gastric Mucosal Barrier", Arzneim.-Forsch., vol. 39(I), No. 5 (1989), pp. 590–592.

Gabor, M. & A. Kekes-Szabo, "Effect of Bioflavoids in Experimental Gastric Ulcer", Kiserletes Orvostudomany, vol. 24, (1972), pp. 1–4.

Goel, R. K., V. B. Pandey, S. P. D. Dwivedi & Y. V. Rao "Antiinflammatory and Anti-Ulcer Effects of Kaempferol, a Flavone, isolated from *Rhamnus procumbens*", Indian Journal of Experimental Biology, vol. 26 (Feb. 1988), pp. 121–124.

Hatamaya, K. S. Yokomori, Y. Kawashima, R. Saziki & K. Kyogoku, "Anti-Ulcer Effect of Isoprenyl Flavonoids. III. Synthesis and Anti-Ulcer Activity of Metabolites of 2'Carboxymethoxy-4,4'—bis(3-methyl-2-butenyloxy)chalcone" Chemical & Pharmaceutical Bulletin, vol. 33, No. 4 (Apr., 1985)), 1327–1333.

Ilarionov, I., L. Rainova & N. Nakov, "On the Antiinflammatory and Antiulcer Activity of Some Flavonoids Isolated from the Genus Genista L.", Farmatsiya (Sofia), vol. 29, No. 6 (1979), pp. 39–46.

Konturek, S. J., M. E. Kitler, T. Brzozowski & T. Radecki, "Gastric Protection by Meciadanol—A New Synthetic Flavonoid-Inhibiting Histidine Decarboxylase", Digestive Diseases and Sciences, vol. 31, No. 8 (Aug. 1986), pp. 847–852.

Konturek, S. J., T. Radecki, T. Brzozowski, D. Drozdowicz, I. Piastucki, M. Muramatsu, M. Tanaka & H. Aihara, "Antiulcer and Gastroprotective Effects of Solon, a Synthetic Flavonoid Derivative of Sophoradin. Role of Endogenous Protaglandins", European Journal of Pharmacology, vol. 125, (1986), pp. 185–192.

Konturek, S. J., T. Mrzozowski, D. Drozdowicz, W. Pawlik, & R. Sendur, "Gastro-protective and Ulcer Healing Effects of Sonon, A Synthetic Flavonoid Derivative of Sophoradin", Hepato-Gastroenterology, vol. 34 (1987, pp. 164–170. Prostaglandins, European Journal of Pharmacology, vol. 125, (1986), pp. 185–.

(List continued on next page.)

OTHER PUBLICATIONS

Kyogoku, K., K. Hatayama, S. Yokomori, R. Saziki, S. Nakane, M. Sasajima, J. Sawada, M. Ohzeki & I. Tanaka, "Anti-ulcer Effect of Isoprenyl Flavonoids, II. Synthesis and Anti-ulcer Activity of New Chalcones Related to Sophoradin", Chemical & Pharmaceutical Bulletin, vol. 27, No. 12 (1979), pp. 2943–2953.

Lin, Y. L. & S. Y. Hsu, "The Constituents of the Anti-ulcer Fractions of *Euphorbia Hirta*", The Chinese Pharmaceutical Journal, vol. 40, No. 1 (1988), pp. 49–51.

Martin, M. J., C. Alarcon de la Lastra, E. Marhuenda, F. Delgado & J. Torreblanca, "Anti-ulcergenicity of the Flavonoid Fraction from *Dittrichia viscosa* (L.) W. Greuter in Rats", Pythotherapy Research, vol. 2, No. 4 (1988), pp. 183–186.

Martindale The Extra Pharmacopoeia, 28th Ed., p. 1704, Item 12667-x (1983).

Middleton, E. & G. Drzewiecki, "Flavonoid Inhibition of Human Basophil Histamine Release Stimulated by Various Agents", Biochemical Pharmacology, vol. 33, No. 21 (1984), pp. 3333–3338.

Mower, R. L., R. Landolfi & Steiner, "Inhibiiton In Vitro of Platelet Aggregation and Arachidonic Acid Metabolism by Flavone", Biochemical Pharmacology, vol. 33, No. 3, (1984), pp. 357–363.

Obolentseva, G. V. & Y. I. Khadzhai, "Pharmacological Data on Certain Aspects of the Action of Licorice (*Glycyrrhiza Glabra*) Flavonoids", Vop. Izuch. Ispol'z. Solodki Nauka. (1966), pp. 163–166.

Parmer, N. S. & M. N. Ghosh, "The Anti-Inflammatory and Anti-Gastric Ulcer Activities of Some Bioflavonoids", Bull. Jawaharlal Inst. Post-Grad. Med. Educ. Res., vol. 1, No. 1 (1976), pp. 6–11.

Parmer, N. S. & G. Hennings, "The Gastric Antisecretory Activity of 3-Methoxy-5,7,3', 4'-tetrahydroxy-flavan (ME)—A Specific Histidine Decarboxylase Inhibitor in Rats", Agents and Actions, vol. 15, No/ 3/4 (1984), pp. 143–145.

Pfister, J. R., W. E. Wymann, M. E. Schuler & A. P. Roskowski, "Inhibition of Histamine-Induced Gastric Secretion by Flavone-6-carboxylic Acids", J. Med. Chem., vol. 23 (1980, pp. 335–338.

Rainova, L., N. Nakov, S. Bogdanova, E. Minkov & D. Staneva-Stoicheva, "Ulcero-protective Activity of the Flavonoids of *Genista Rumelica* " Vel. Phytotherapy Research, vol. 2, No. 3 (1988), pp. 137–139.

Selenina, L. V., R. N. Zozulya & T. N. Yakovleva, "Polyphenols of *Potentilla Erecta* and Their Biological Activity", Rast. Resur., vol. 9, No. 3 (1973), pp. 409–414.

Tariq, M., N. S. Parmar, A. M. Ageel, I. A. Al-Meshal & A. R. Abu-Jayyab, "The Gastric Anti-Ulcer Activity of Khat (*Catha edulis* Forsk): Investigations on its Flavonoid Fraction", Research Communications in Substances Abuse, vol. 5, No. 2 (1984), pp. 157–160.

Villar, A., M. A. Gasco & M. J. Alcaraz, "Anti-inflammatory and Anti-ulcer Properties of Hypolaetin-8--glucoside, a Novel Plant Flavonoid", J. Pharm. Pharmacol., vol. 36 (1984), pp. 820–823.

Viswanthan, S., P. Kulanthaivel, S. K. Nazimudeen, T. Vinayakam, C. Gopalakrishnan & L. Kameswaran, "The Effect of Apigenin 7,4'-Di-O-Methyl Ether, a Flavone from *Andrographis Paniculata* on Experimentally Induced Ulcers" Indian J. Pharm. Sci., vol. 43, No. 5 (1981), pp. 159–161.

Yamahara, J., M. Mochizuki, T. Chisaka, H. Fujimura & Y. Tamai, "The Antiulcer Action of Sophora and the Active Constituent in Sophora II. The Antiulcer Action of Vexibinol", Chem. Pharm. Bull., vol. 38, No. 4 (1990), pp. 1039–1044.

1991 Drugs Available Abroad, Derwent Publications Ltd., London, England, pp. 298–299, Item 298.

USE OF FLAVONE DERIVATIVES FOR GASTROPROTECTION

This is a continuation-in-part of application Ser. No. 07/878,582, filed on May 5, 1992, now abandoned.

TECHNICAL FIELD

The subject invention relates to flavone and certain substituted flavones which are useful as gastroprotective agents.

BACKGROUND OF THE INVENTION

Hemorrhages and perforations of the mucosal lining of the gastro-intestinal tract are serious medical concerns. Such disorders are often associated with stress and with the ingestion of certain drugs, particularly nonsteroidal anti-inflammatory drugs (NSAIDs) and/or ethanol. New and improved methods for treating disorders such as gastric ulcers, duodenal ulcers, peptic ulcer disease, and non-ulcer dyspepsia are needed. In particular, new methods are needed for a safe and effective gastroprotective therapy for chronic users of NSAIDs. NSAIDs which can cause damage to the mucosal lining of the gastrointestinal tract include, but are not limited to aspirin and other salicylates, ibuprofen, ketoprofen, naproxen, ketorolac, flurbiprofen, piroxicam, meclofenamate sodium, phenylbutazone, sulindac, difunisal, indomethacin, etodolac, fenoprofen calcium, mefenamic acid, tolmetin sodium and diclofenac sodium.

The following references disclose certain compounds related to flavone having various effects on the gastrointestinal system; some are disclosed to have anti-ulcer activity: Belgian Patent No. 888,982 of Fabrica Espanola de Productos Quimicos y Farmaceutics, S. A., published Sep. 16, 1981; Japanese Patent No. 70-24111 of Taisho Pharmaceutical Co., Ltd., published Nov. 10, 1972; Japanese Patent No. 72-32888 of Taisho Pharmaceutical Co., Ltd., published Dec. 15, 1973; Japanese Patent No. 72-032889 of Taisho Pharm. Co., published Dec. 15, 1973; Japanese Patent No. 74-093023 of Taisho Pharmaceutical KK, published Feb. 24, 1976; Japanese Patent Application No. 78-098452 of Taisho Pharmaceutical KK, published Feb. 27, 1980; French Patent No. 011,196 of Fabrica Espanola de Productos Quimicos y Farmaceutics, S. A., published Nov. 10, 1980; Swiss Patent No. 126,197 of Khark Chem. Pharm., published May 13, 1977; German Patent No. 615,710 of Hoechst AG, published Nov. 11, 1987; Obolentseva, G. V. & Y. I. Khadzhai, "Pharmacological Data on Certain Aspects of the Action of Glycyrrhiza Flavonoids", *Vop. Izuch. Ispol'z. Solodki Nauka.* (1966), pp. 163–166; Gabor, M. & A. Kekes-Szabo, "Effect of Bioflavonoids in the Experimental Gastric Ulcer", Kiserl. Orvostud., Vol. 24, No. 1 (1972), pp. 1–4; Ciaceri, G. & G. Attaguile, "Effects of Luteolin, Apigenin, and Acacetin on Experimentally Induced Gastric Ulcer", *Minerva Med.*, Vol. 63, No. 29 (1972), pp. 1665–1668; Selenina, L. V., R. N. Zozulya & T. N. Yakovleva, "Polyphenols of Potentilia Erecta and Their Biological Activity", Rast. Resur., Vol. 9, No. 3 (1973), pp. 409–414; Parmar, N. S. & M. N. Ghosh, "The Anti-Inflammatory and Anti-Gastric Ulcer Activities of Some Bio flavonoids", *Bull. Jawaharlal Inst. Post-Grad. Med. Educ. Res.*, Vol. 1, No. 1 (1976), pp. 6–11; Pfister, J. R., W. E. Wymann, M. E. Schuler & A. P. Roszkowski, "Inhibition of Histamine-Induced Gastric Secretion by Flavone-6-carboxylic Acids", *J. Med. Chem.*, Vol. 23 (1980), pp. 335–338; Ilarionov, I., L. Rainova & N. Nakov, "Antiinflammatory and Antiulcer Effect of Some Flavonoids Isolated from the Genus Genista", *Farmatsiya (Sofia)*, Vol. 29, No. 6 (1979), pp. 39–46; Viswanthan, S., P. Kulanthaivel, S. K. Nazimudeen, T. Vinayakam, C. Gopalakrishnan & L. Kameswaran, "The Effect of Apigenin 7,4'-Di-O-Methyl Ether, a Flavone from Andrographis Paniculata on Experimentally Induced Ulcers", *Indian J. Pharm. Sci.*, Vol. 43, No. 5 (1981), pp. 159–161; Barnaulov, O. D., O. A. Manicheva, G. G. Zapesochnaya, V. L. Shelyuto & V. I. Glyzin, "Effect of Some Flavonoids on the Ulcerogenic Activity of Reserpine in Mice", *Khim.-Farm. Zh.*, Vol. 16, No. 3 (1982), pp. 300–303; Barnaulov, O. D., O. A. Manicheva & P. P. Denisenko, "Method for Evaluating the Effect of Preparations on the Ulcerogenic Activity of Reserpine in Mice", *Farmakol. Toksikol. (Moscow)*, Vol. 45, No. 4 (1982), pp. 105–110; Tariq, M., N. S. Parmar, A. M. Ageel, I. A. AI-Meshal & A. R. Abu-Jayyab, "The Gastric Anti-Ulcer Activity of Khat (Catha edulis Forsk): Investigations on its Flavonoid Fraction", *Research Communications in Substances of Abuse*, Vol. 5, No. 2 (1984), pp. 157–160; Villar, A., M. A. Gasco & M. J. Alcaraz, "Antiinflammatory and Anti-ulcer Properties of Hypolaetin-8-glucoside, a Novel Plant Flavonoid", *J. Pharm. Pharmacol.*, Vol. 36 (1984), pp. 820–823; Barnaulov, O. D., O. A. Manicheva & N. F. Komissarenko, "Comparative Evaluation of the Effect of Some Flavonoids on Changes in the Gastric Wall of Reserpine-Treated or Immobilized Mice", *Khim.-Farm. Zh.*, Vol. 17, No. 8 (1983), pp. 946–951; Barnaulov, O. D., O. A. Manicheva, V. L. Shelyuto, M. M. Konopleva & V. I. Glyzin, "Effect of Flavonoids on the Development of Experimental Dystrophy of the Stomach in Mice", *Khim.-Farm. Zh.*, Vol. 18, No. 8 (1984), pp. 935–941; Barnaulov, O. D., O. A. Manicheva, I. I. Chemesova & N. F. Komissarenko, "Comparative Evaluation of the Effect of Flavonoids on the Development of Experimental Lesions in the Mouse Stomach", *Khim.-Farm. Zh.*, Vol. 18, No. 11 (1984), pp. 1330–1333; Barnaulov, O. D., O. A. Manicheva, R. K. Yasinov & G. P. Yakovlev, "Evaluation of the Effect of Flavonoids from the Aerial Parts of Astragalus Quisqualis Bunge and A. Floccosifolius Sumn. on the Development of Experimental Lesions in the Mouse Stomach", *Rastit. Resur.*, Vol. 21, No. 1 (1985), pp. 85–90; Konturek, S. J., M. E. Kitler, T. Brzozowski & T. Radecki, "Gastric Protection by Meciadanol—A New Synthetic Flavonoid-Inhibiting Histidine Decarboxylase", *Digestive Diseases and Sciences*, Vol. 31, No. 8 (Aug. 1986), pp. 847–852; Goel, R. K., V. B. Pandey, S. P. D. Dwivedi & Y. V. Rao, "Antiinflammatory and Anti-ulcer Effects of Kaempferol, a Flavone, Isolated from Rhamnus procumbens", *Indian Journal of Experimental Biology*, Vol. 26 (February 1988), pp. 121–124; Rainova, L., N. Nakov, S. Bogdanova, E. Minkov & D. Staneva-Stoicheva, Phytotherapy Research, Vol. 2, No. 3 (1988), pp. 137–139; Lin, Y. L. & S. Y. Hsu, "The Constituents of the Antiulcer Fractions of Euphorbia Hirta", *The Chinese Pharmaceutical Journal*, Vol. 40, No. 1 (1988), pp. 49–51; Martin, M. J., C. Alarcon de la Lastra, E. Marhuenda, F. Delgado & J. Torrebianca, "Anti-ulcerogenicity of the Flavonoid Fraction from Dittrichia viscosa (L.) W. Greuter in Rats", *Phytotherapy Research*, Vol. 2, No. 4 (1988), pp. 183–186; Cristoni, A., S. Malandrino & M. J. Magistretti, "Effect of a Natural Flavonoid on Gastric Mucosal Barrier", *Arz-* neim.-Forsch., Vol. 39(I), No. 5 (1989), pp. 590–592; Brasseur, T., "Proprietes Anti-inflammatoires de Flavonoides", J. Pharm. Belg., Vol. 44, No. 3 (1989), pp. 235–241.

It is an object of the subject invention to provide methods of using certain substituted flavone compounds as gastroprotective agents.

It is a further object of the subject invention to use such compounds particularly for protection against NSAID-induced damage to the gastric lining.

It is also an object of the subject invention to provide compositions comprising certain substituted flavone compounds for use as gastroprotectants.

SUMMARY OF THE INVENTION

The subject invention relates to methods for preventing or treating damage to the mucosal lining of the gastrointestinal tract of a human or lower animal by administering a safe and effective amount of a compound having the structure:

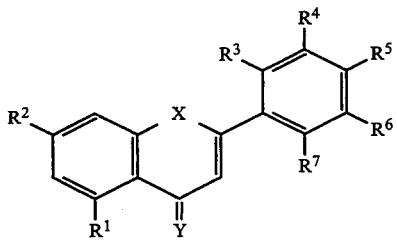

wherein X and Y are each independently selected from O and S; $R^1$, $R^2$ and $R^3$ are each independently selected from hydrogen, hydroxy, halo, unsubstituted or monosubstituted straight or branched $C_1$–$C_4$ alkanyl, and unsubstituted or monosubstituted straight or branched $C_1$–$C_4$ alkanoxy; and each of $R^4$, $R^5$, $R^6$ and $R^7$ is hydrogen or, if one or more of $R^1$, $R^2$ and $R^3$ is other than hydrogen, each of $R^4$, $R^5$, $R^6$ and $R^7$ is selected from hydrogen halo, trifluoromethyl, and unsubstituted straight or branched $C_1$–$C_4$ alkanyl.

DETAILED DESCRIPTION OF THE INVENTION

The references disclosed above disclose a variety of different effects on the gastrointestinal system achieved by administration of certain flavonoid-type compounds. Because such effects are varied and uncertain for different narrow groups of flavonoid compounds, whether or not certain flavonoid-type compounds will have any gastrointestinal effect, and if so, what the effect will be, is not predictable prior to testing the compounds.

The subject invention involves compounds related to flavone having the chemical structure:

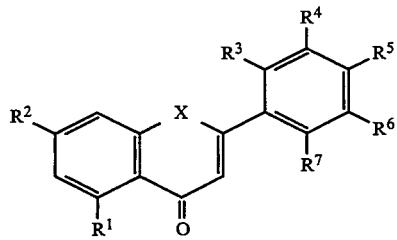

(1)

In Structure (1), X and Y are independently selected from oxygen and sulfur. Preferably at least one of X and Y is oxygen. More preferably both X and Y are oxygen; also more preferably Y is oxygen and X is sulfur.

In Structure (1), each of $R^1$, $R^2$ and $R^3$ is independently selected from hydrogen; hydroxy; halo; unsubstituted or monosubstituted, straight or branched $C_1$–$C_4$ alkanyl (saturated alkyl); and unsubstituted or monosubstituted, straight or branched $C_1$–$C_4$ alkanoxy (saturated alkoxy). Preferred substituents of alkanyl and alkanoxy moieties include hydroxy, halo, carboxy, and $C_1$–$C_4$ (especially $C_2$) esters of carboxy; more preferred still is carboxy and $C_1$–$C_2$ esters of carboxy. Also preferred is unsubstituted alkanyl or alkanoxy $R^1$, $R^2$ and $R^3$ moieties.

$R^1$ is preferably selected from hydrogen, fluoro, methoxy, and carboxymethoxy and its methyl and ethyl esters. More preferred $R^1$ is hydrogen or methoxy, especially methoxy. Also more preferred $R^1$ is carboxymethoxy or its methyl or ethyl ester, especially ethoxycarbonylmethoxy.

Preferred $R^2$ is selected from hydrogen, methoxy, ethoxy, methyl, carboxymethoxy and its methyl and ethyl esters. More preferred $R^2$ is hydrogen. When $R^1$ is other than hydrogen, more preferred $R^2$ is hydrogen or methoxy, especially when $R^1$ is methoxy.

Preferred $R^3$ is selected from hydrogen, hydroxy, methoxy, methyl, chloro and fluoro. More preferred $R^3$ is hydrogen or fluoro. Also more preferred $R^3$ is methoxy.

In Structure (1), each of $R^4$, $R^5$, $R^6$ and $R^7$ is hydrogen; or, if one of $R^1$, $R^2$ and $R^3$ is other than hydrogen, each of $R^4$, $R^5$, $R^6$ and $R^7$ is selected from hydrogen, halo, trifluoromethyl and unsubstituted straight or branched $C_1$–$C_4$ alkanyl.

Preferred $R^4$ is hydrogen. When one or more of $R^1$, $R^2$ and $R^3$ is other than hydrogen; particularly when $R^1$ is other than hydrogen, especially methoxy, and $R^2$ is hydrogen or methoxy, especially hydrogen, and $R^3$ is hydrogen; preferred $R^4$ is selected from hydrogen, fluoro, chloro and trifluoromethyl.

Preferred $R^5$ is hydrogen. When one or more of $R^1$, $R^2$ and $R^3$ is other than hydrogen; particularly when $R^1$ is other than hydrogen, especially methoxy, and $R^2$ is hydrogen or methoxy, especially hydrogen, and $R^3$ is hydrogen; preferred $R^5$ is selected from hydrogen, methyl, fluoro and chloro.

Preferred R6 is hydrogen. When one or more of $R^1$, $R^2$, and $R^3$ is other than hydrogen; particularly when $R^1$ is other than hydrogen, especially methoxy, and $R^2$ is hydrogen or methoxy, especially hydrogen, and $R^3$ is hydrogen, preferred $R^6$ is selected from hydrogen, fluoro and chloro.

In Structure (1), preferably no more than two of $R^3$, $R^4$, $R^5$, $R^6$ and $R^7$ are other than hydrogen; more preferably no more than one of $R^3$, $R^4$, $R^5$, $R^6$ and $R^7$ is other than hydrogen. If two of $R^3$, $R^4$, $R^5$, $R^6$ and $R^7$ are other than hydrogen, they are preferably bonded to non-adjacent carbon atoms; more preferably they are $R^3$ and $R^5$ or $R^4$ and $R^6$.

When $R^1$ is other than hydrogen, especially when $R^1$ is methoxy, more preferred $R^2$ is hydrogen or methoxy, more preferred $R^3$ is hydrogen or fluoro or chloro, more preferred $R^4$ is hydrogen or trifluoromethyl, more preferred $R^5$ is hydrogen or fluoro or chloro, and more preferred $R^6$ and $R^7$ are hydrogen; more preferably still no more than one of $R^3$, $R^4$, $R^5$, $R^6$ and $R^7$ is other than hydrogen.

When $R^2$ is other than hydrogen, especially when $R^2$ is methoxy, preferred $R^1$ is hydrogen or methoxy, preferred $R^3$ is hydrogen or fluoro or chloro, and preferred $R^4$, $R^5$, $R^6$ and $R^7$ are all hydrogen.

When $R^3$ is other than hydrogen, especially when $R^3$ is fluoro or chloro, preferred $R^1$ is hydrogen or methoxy, especially hydrogen, preferred $R^2$ is hydrogen or methoxy, especially hydrogen, and preferred $R^4$, $R^5$, $R^6$ and $R^7$ are all hydrogen.

The term "Compound", as used herein, refers to a compound of Structure (1). Structure (1) depicts the compound flavone when both X and Y are oxygen and all of $R^1$, $R^2$, $R^3$, $R^4$, $R^5$, $R^6$ and $R^7$ are hydrogen. Substitution positions for flavone, as used in naming compounds herein, are as depicted in the following structure:

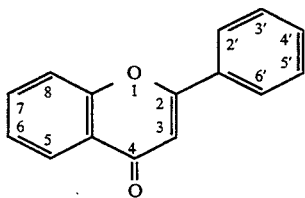

Particularly preferred compounds useful in the subject invention are selected from flavone, 1-thioflavone, 5-methoxyflavone, 5-isopropoxyflavone, 5-butoxyflavone, 5-fluoroflavone, 7-methoxyflavone, 7-methylflavone, 7ethoxyflavone, 2'-hydroxyflavone, 2'-methoxyflavone, 2'-methylflavone, 2'-fluoroflavone, 4'-fluoro-5-methoxyflavone, 3'-trifluoromethyl-5-methoxyflavone, 2'-chloro-5-methoxyflavone, 4'-methyl-5-methoxyflavone, 4'-chloro-5-methoxyflavone, 5,7-dimethoxyflavone, 5-carboxymethoxyflavone, 7-carboxymethoxyflavone, 5-ethoxycarbonylmethoxyflavone, 7-ethoxycarbonylmethoxyflavone, 4'-fluoro-7-methoxyflavone and 2'-chloro-7-methoxyflavone. More preferred compounds useful in the subject invention include flavone, 1-thioflavone, 5-methoxyflavone, 5-fluoroflavone, 7-methylflavone, 4'-fluoro-5-methoxyflavone, 4'-chloro-5-methoxyflavone, 4'-methyl-5-methoxyflavone, 3'-trifluoromethyl-5-methoxyflavone, 5-ethoxycarbonylmethoxyflavone, 5,7-dimethoxyflavone, 2'-fluoroflavone, and 2'-methylflavone. Especially preferred compounds useful in the subject invention include 1-thioflavone, 2-fluoroflavone, 5,7-dimethoxyflavone, 4'-fluoro-5-methoxyflavone, and 4'-chloro-5-methoxyflavone; also especially preferred is 5-methoxyflavone.

METHODS OF USE

The subject invention involves methods for treating or preventing gastrointestinal disorders in humans or lower animals by administering, to a human or lower animal in need of such treatment or prevention, a safe and effective amount of a Compound. The Compounds provide protection against damage to the mucosal lining of the gastrointestinal tract, especially of the esophagus, the stomach, and the duodenum, particularly of the stomach. Gastrointestinal disorders which can be treated or prevented by avoiding damage to the mucosal lining include, one or more of gastritis, non-ulcer dyspepsia, gastroesophageal reflux disease, esophagitis, gastric ulcers, duodenal ulcers, Zolinger-Ellison Syndrome, stress-induced damage, ethanol-induced damage, NSAID-induced damage, and damage induced by other drugs. Of particular interest is the prevention of NSAID-induced damage and stress-induced damage.

The phrase "safe and effective amount", as used herein, means an amount of a material high enough to significantly modify the condition to be treated in a positive way, but low enough to avoid serious side effects (at a reasonable benefit/risk ratio) within the scope of sound medical judgment. The safe and effective amount of a material will vary with the particular condition being treated, the age and physical condition of the patient being treated, the severity of the condition, the duration of the treatment, the nature of concurrent therapy, the specific composition employed, the particular pharmaceutically-acceptable carrier utilized, and like factors within the knowledge and expertise of the attending physician.

While the methods of the subject invention are not limited to any single mechanism of action, it is believed that the subject gastroprotective agents provide protection for the gastric lining via enhancement of mucosal blood flow and vascular integrity. Mucosal blood flow supplies oxygen, bicarbonate, and nutrients to mucosal cells involved in maintaining a trans epithelial barrier to acid and pepsin.

The Compounds provide gastroprotective activity primarily through systemic means. Consequently, modes of administering the Compounds which achieve effective systemic levels of the Compounds will provide the desired gastroprotective activity. Such means of administration include, but are not limited to, peroral and parenteral. The preferred route of administration is peroral.

The methods of the subject invention include administering to a human or lower animal a composition comprising a Compound. The dose of Compound per administration is preferably from about 0.1 mg/kg to about 100 mg/kg of body weight, more preferably from about 0.4 mg/kg to about 25 mg/kg, more preferably still from about 1 mg/kg to about 10 mg/kg, still more preferably from about 2 mg/kg to about 4 mg/kg.

The frequency of administering the above amounts of Compound is preferably from about every other day to about four times daily, more preferably from about once daily to about thrice daily, more preferably still from about once daily to about twice daily.

COMPOSITIONS

Another aspect of the subject invention involves compositions comprising a Compound and a pharmaceutically-acceptable carrier.

Preferred compositions are those in dosage forms intended for peroral administration. Fluid dosage forms for oral administration include suspensions, emulsions and the like. Solid dosage forms for oral administration include tablets, capsules, powders, lozenges, and the like.

Preferred compositions are also those in dosage forms intended for parenteral administration. Fluid dosage forms for parenteral administration include solutions, suspensions, emulsions and the like.

The Compounds generally have very low solubility in aqueous media. In order to attain effective systemic levels of the Compounds, it is preferred that the compositions of the subject invention comprise the Compound where the Compound exists in a form having a small particle size. The form of the composition may be a solid mixture, encapsulated solid mixture, solid dispersion, suspension of solid particles in liquid, emulsion, or the like.

In the compositions of the subject invention, the Compound preferably is in a solid, particulate form with 95% (by weight) having a particle size of less than about 100 μm, more preferably with 95% having a particle size of less than about 50 μm, more preferably still with 95% having a particle size of less than about 10 μm. Particle size is determined by, e.g., use of a Coulter counter, Coulter Electronics Ltd., Beds, U.K.

In the compositions of the subject invention, the Compound preferably comprises from about 1% to about 99% of the composition, more preferably from about 10% to about 90%, more preferably still from about 40% to about 70%.

Since a preferred use of certain Compounds is to prevent or treat drug-induced damage to the mucosal lining, compositions of the subject invention include those comprising an effective Compound and a drug which may induce such damage. Preferred compositions comprise such Compound and a NSAID, particularly a NSAID listed hereinabove, especially naproxyn or ketorolac. In such compositions, the NSAID preferably comprises from about 10% to about 80% of the composition, more preferably from about 20% to about 60%, more preferably still from about 30% to about 50%.

The term "pharmaceutically-acceptable carrier", as used herein, means one or more compatible solid or liquid filler diluent or encapsulating substance which is suitable for administration to a human or lower animal. The term "compatible", as used herein, means that the components of the pharmaceutical carrier are capable of being commingled with the Compounds, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the human or lower animal being treated.

Some examples of the types of substances which can serve as components of pharmaceutically-acceptable carriers include the following: diluents such as starch, microcrystalline cellulose, lactose, dicalcium phosphate, calcium sulfate, mannitol and sucrose; binders and adhesives such as acacia, tragacanth, gelatin, methylcellulose, hydroxypropyl methylcellulose, and polyvinylpyrrolidone; disintegrants such as starch, pregelatinized starch, sodium starch glycolate, alginates, crospovidone, and croscarmellose sodium; lubricants such as stearic acid, stearate salts, and polyethylene glycol; glydants such as talc and fumed silica; solvents such as water, vegetable oils, alkyl esters, mineral oil, sorbitol, glycerin, polyethylene glycol, propylene glycol and ethanol; emulsifying and wetting agents such as polyoxyethylene alkyl ethers, polyoxyethylene castor oil derivatives, polyoxyethylene sorbitan fatty acid esters, polyoxyethylene stearates, sorbitan esters, and sodium alkyl sulfates; other specialty materials such as preservatives, buffering agents, colorants, flavors, sweeteners, antioxidants, and other stabilizers.

The following are examples of compositions of the subject invention. They are not intended to be limiting with regard to useful compositions, since it is clear that the foregoing disclosure supports a wider range of compositions than exemplified hereinbelow.

EXAMPLE I

A tablet composition of the subject invention consists of the following:

| Ingredient | Amount per Tablet (mg) |
| --- | --- |
| 5-Methoxyflavone | 150 |
| Microcrystalline Cellulose | 200 |
| Pregelatinized Starch | 100 |
| Crospovidone | 10 |
| Magnesium Stearate | 5 |

All ingredients are dry blended except magnesium stearate. The magnesium stearate is added and blended briefly. Tablets are made from the resulting blend by conventional tableting means.

EXAMPLE II

A tablet composition of the subject invention consists of the following:

| Ingredient | Amount per Tablet (mg) |
| --- | --- |
| Micronized 4'-fluoro-5-methoxyflavone (particle size: >95% <10μ) | 200 |
| Microcrystalline Cellulose | 50 |
| Pregelatinized Starch | 100 |
| Providone | 10 |
| Sodium Starch Glycolate | 20 |
| Stearic Acid | 8 |

The providone is dissolved in an appropriate amount of water. The 4'-fluoro-5-methoxyflavone, microcrystalline cellulose, and half of sodium starch glycolate are added to the providone solution. The mixture is granulated and dried. The remaining sodium starch glycolate and stearic acid are added and blended briefly. Tablets are made from the resulting blend by conventional tableting means.

EXAMPLE III

A capsule composition of the subject invention consists of the following:

| Ingredient | Amount per Capsule (mg) |
| --- | --- |
| Micronized 7-Methoxyflavone (particle size: >95% <10μ) | 100 |
| Starch | 50 |
| Croscarmellose Sodium | 5 |
| Fumed Silica | 5 |

All ingredients are dry blended. The resulting blend is filled into hard gelatin capsules by conventional means.

EXAMPLE IV

An oral suspension of the subject invention consists of the following:

| Ingredient | Amount (%) |
| --- | --- |
| Micronized 5-Carboxymethyoxyflavone (particle size: >95% <10 m) | 15.0 |
| Colloidal Magnesium Aluminum Silicate | 1.0 |
| Methyl Cellulose | 0.5 |
| Glycerin | 5.0 |
| Sodium Saccharin | 0.1 |

-continued

| Ingredient | Amount (%) |
| --- | --- |
| Flavor | 1.0 |
| Polysorbate 80 | 2.0 |
| Methylparaben | 0.2 |
| Propylparaben | 0.1 |
| Purified Water | q.s. |

The colloidal magnesium aluminum silicate and parabens are added to about one-third of the water at about 90° C.; the resulting mixture is milled and cooled. Methylcellulose is added to the remaining water and allowed to dissolve. The colloidal magnesium aluminum silicate mixture, polysorbate 80, and glycerin are then added to the aqueous methyl cellulose solution followed by glycerin, polysorbate and the 5-carboxymethoxyflavone. After dispersion of the active, flavor and sodium saccharin are added with stirring.

The gastroprotective activity of the Compounds is determined using the following methods.

Test Method I

Ethanol-Induced Gastric Damage Model

Animals: Male CD (Sprague-Dawley) rats (150–175 grams) are supplied by the Charles River Breeding Laboratories, Kingston, N.Y. Upon receipt, rats are double-housed in stainless steel mesh-bottom cages with access to automatic water and Purina rat chow (pellets). Animals are allowed to acclimate for a minimum of 5 days prior to use.

Test Solutions: A stock solution of 1% methyl cellulose (M352-500, Fisher Chemical Co., Fair Lawn, N.J.) is prepared in deionized water and refrigerated. Test Compounds are dosed in a polyethylene glycel-200/1% methyl cellulose in water vehicle (PEG/MC) (PEG-200, Aldrich Chemical Co., Milwaukee, WI). Dose Compound preparations are prepared 30–60 minutes prior to the start of the experiment. A 5% Compound solution or suspension in PEG-200 (w/w) is made for each Compound by combining the components and heating. The required amount of this solution or suspension is weighed into 1% aqueous MC solution for the desired mg/kg dose. The PEG-MC-test Compound mixture is probe sonicated to achieve a uniform suspension of reduced particle size. The resulting solution or suspension is kept homogeneous during dosing by magnetic stirring.

Experimental Procedure: Rats, weighing approximately 250 grams, are weighed, single-housed, food fasted overnight with water supplied ad libitum, and tailcupped to prevent coprophagy. Test Compounds are administered to conscious rats by intraperitoneal (i.p.) injection (1 ml/rat). One hour later, rats receive 1 ml of 100% ethanol administered orally by gastric intubation using a small nethalon catheter (8 French). One hour after ethanol challenge, rats are anesthetized by placing in a chamber filled with carbon dioxide. Rats are then euthanized by cervical dislocation. Stomachs are removed and opened along the greater curvature. Contents are rinsed away with 0.9% saline and placed into individual vials containing saline until lesion measurements are taken.

Lesion Analysis: Gastric damage is assessed by one of two methods. In both methods the stomach is flattened on a small card with mucosal surface up. Total lesion length is determined using the Zeiss Interactive Digitizing Analysis System (ZIDAS). This instrument converts cursor-traced lesions viewed under a dissecting microscope to millimeters (mm) using an internal conversion analysis. The other method determines total area damaged by using the Optimas Image System. This system acquires pictures of each stomach and then the program determines the total area damaged.

Statistics: The mean, standard deviation and standard error of the mean is determined for each treatment group. Percent protection is determined by the formula: 1- (Treatment group mean lesion length or damage area/Control group mean lesion length or damage area)×100. The significance of protection for each treatment is determined by the Student's t-test.

Test Method II

Acute NSAID-Induced Gastric Damage Model

Animals: Rats are male Sprague Dawley from Charles River Breeding Laboratories. Approximate weight range is 200–350 gm. Before using the rats in an experiment, they are acclimated at least two days in the test facility. Rats are double housed in stainless steel mesh bottomed cages with access to pelletized rat chow and tap water.

Animal Preparation: Rats are weighed and tailcupped to prevent coprophagy mid to late afternoon on the day prior to the experiment. All weights are recorded to determine mean weight for mg/kg dosing calculations. After tailcupping, rats are single housed and food fasted. Water is ad libitum throughout the night and through the experiment. Rats are assigned to dose groups and identified.

Chemical/Drug Sources: Test Compounds are purchased or synthesized. Tween 20 and Tween 80 are polyoxyethylenesorbitan monolaurate and monooleate, respectively, and are purchased from Sigma Chemical Company. Poly(ethylene glycol), (PEG-200), is purchased from Aldrich Chemical Company. Methyl cellulose-4000 centipoise (MC), is purchased from Fisher Chemical Company. NSAID, e.g. indomethacin, acetylsalicylic acid, is purchased.

Drug Preparation: NSAID to be dosed by oral (p.o.) gavage is prepared the morning of the experiment. The NSAID dose, e.g., 20 mg/kg for indomethacin, 100 mg/kg for acetylsalicylic acid, is prepared for each rat in 1-ml volume per rat according to the mean rat weight determined at tailcupping. The appropriate amount of NSAID is weighed into a vial and diluted in an aqueous vehicle with suitable surfactant (Tween) and, if necessary, MC to provide a stable preparation of the NSAID, e.g., a vehicle of 0.5% methyl cellulose (MC)-2.0% Tween 20 for indomethacin, or 0.75% Tween 80 for acetylsalicylic acid. This preparation is sonicated in a bath sonicator for 20 minutes prior to dosing. During dosing the preparation is stirred constantly, if necessary. Alternatively, NSAID, e.g., indomethacin to be dosed by subcutaneous (s.c.) or intraperitoneal (i.p.) injection, is prepared the morning of the experiment. The NSAID dose, e.g., 30 mg/kg for indomethacin, is prepared for each rat in 1-ml volume per rat according to the mean rat weight determined at tailcupping. The appropriate amount of indomethacin is weighed into a vial and diluted with 200 mM sodium bicarbonate, pH 9.00. The pH of the final solution is approximately 8.6. This is stirred until dissolved and bath-sonicated 20 minutes before dosing begins. During dosing the solution is constantly stirred.

Test Compound preparations are prepared the morning of the experiment in PEG-200-1% MC (PEG-MC). The concentration of the dosing solution varies according to each experimental protocol.

A 5-20% solution of the test Compound in PEG-200 is made (w/w) and placed on the hotplate to dissolve or suspend the test Compound and establish a fine, uniform particle size. A portion of this is weighed into 1% MC for the needed mg/ml dose concentration (assuming 1 ml=1 gm MC). The PEG-MC mixture is quickly probe-sonicated for thorough suspension of the test Compound in the methyl cellulose. The suspension is bath-sonicated prior to dosing and magnetically stirred during the experiment. The PEG concentration does not exceed 10% of the dose solution. A standard 1 ml/rat volume is used whenever possible. Greater than 1 ml may be needed to maintain less than 10% PEG in the dosing solution. A rat is dosed no more than 2 ml. This protocol is used for p.o. or i.p. dosing.

Dosing: By any dose route, conscious rats are dosed first with the test Compound preparation; for control groups, the preparation used is vehicle without test Compound. Thirty minutes later rats receive NSAID preparation. Dosing preparations are measured into standard disposable plastic syringes. 8-Fr nelathon catheters are used to reach the stomach for p.o. delivery. 20-Gauge disposable needles are used for i.p. or s.c. dosing. Rats are sacrificed 4 hours after receiving the NSAID.

Sacrifice: Rats are placed in a chamber filled with $CO_2$ gas to put them to sleep. The $CO_2$ source is either dry ice or gas from a 95/5 $CO_2/O_2$ tank. Once asleep, the rats are euthanized by cervical dislocation. The abdomen is opened and the stomach quickly removed. Fat and connective tissue are cleaned from the outer surface and the stomach is cut open along the greater curvature. Stomach contents are rinsed away by dipping the opened stomach into two consecutive beakers of saline. Each stomach is then placed in a vial of saline until all stomachs have been collected.

Stomachs are prepared for lesion measurement by spreading each stomach flat on a card, mucosal surface upward. The cards are placed face down on saran wrap, wrapped to seal the edges, and placed in a −20° C. freezer until lesion measurements can be made.

Lesion Measurement: A few stomachs at a time are removed from the freezer and thawed before reading. Using the Zeiss Interactive Digitizing Analysis System (ZIDAS), lesion length and number are determined for each stomach. The magnification is 2×10 mm. The ZIDAS is calibrated before measurements are done for each experiment using 10-20 measures of 10 mm on a ruler. A scale factor is determined and this is programmed into the ZIDAS for accurate lesion length measurement. The scale factor is accepted when the average of 10-20 measurements of 10 mm falls within the range 9.75 to 10.25 mm. Before lesions can be measured, each stomach is wiped with a Q-tip to remove mucus. Mucus must be removed in order to see the mucosal surface and find the lesions.

Data Processing: Lesion measurements are placed in an Excel spreadsheet. Each treatment group contains two measurements for each stomach, total length of lesions and number of lesions. The mean, standard deviation, and standard error are calculated for each treatment group for both parameters. For each parameter, the percent protection is determined using the mean values by the calculation: % Protection=1-((control-test Compound)/control). A Student's t-test is performed for each test Compound group to determine significance from control (untreated) values for each parameter.

Synthesis Methods

The following synthetic methods can be employed to synthesize the Compounds.

Method A involves a transformation whereby a hydroxyacetophenone is treated with two equivalents of potassium t-butoxide in tetrahydrofuran, followed by addition of an appropriately substituted benzoyl chloride, to form a diketone. Acid-catalyzed cyclization then provides the desired flavone. This chemistry is useful in synthesizing a variety of flavone B-ring analogs.

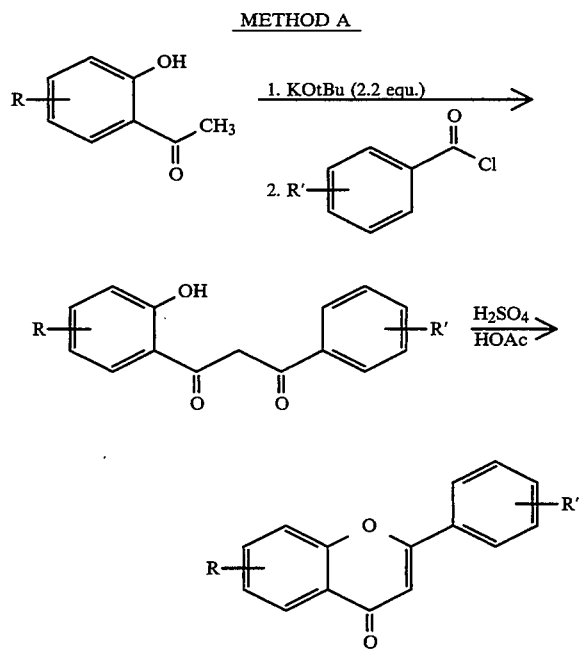

METHOD A

Method B is also employed to synthesize B-ring analogs. This procedure involves sequential treatment of a hydroxyacetophenone with one equivalent of potassium t-butoxide and an appropriately substituted benzoyl chloride, forming a benzoyl ester. To this reaction mixture is added a second equivalent of potassium t-butoxide which affords, after heating, the desired diketone. Acid-catalyzed cyclization provides the desired flavone.

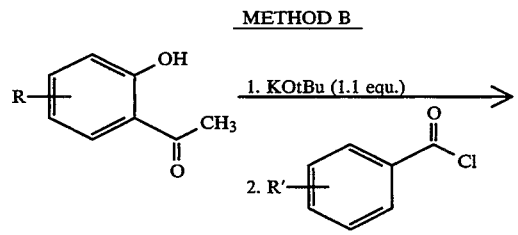

METHOD B

METHOD B -continued

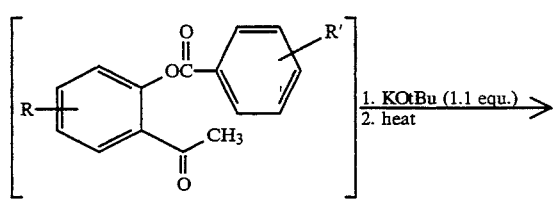

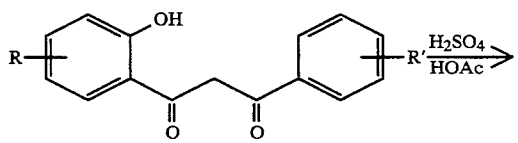

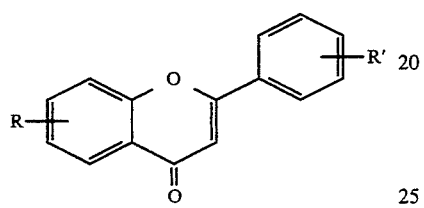

Method C is utilized to synthesize a variety of A-ring substituted flavones. In this process, conjugate addition of the sodium salt of an appropriately substituted phenol to ethyl phenylpropiolate, followed by saponification and intramolecular Friedel Crafts acylation, affords the desired flavone.

METHOD C

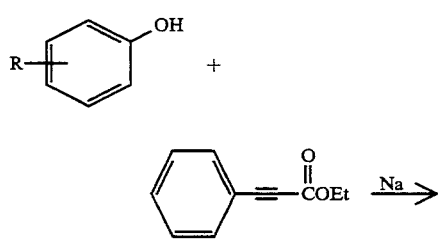

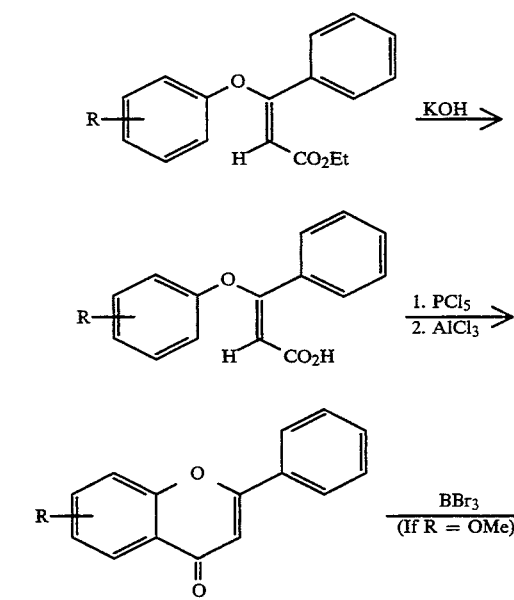

METHOD C -continued

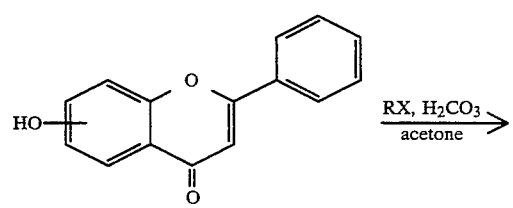

R = OH

Method D is used to synthesize A-ring alkoxy-substituted flavones. Treatment of a hydroxyflavone with an alkyl halide and potassium carbonate in acetone provides alkoxyflavones. Potassium hydroxide is sometimes superior to potassium carbonate as base.

METHOD D

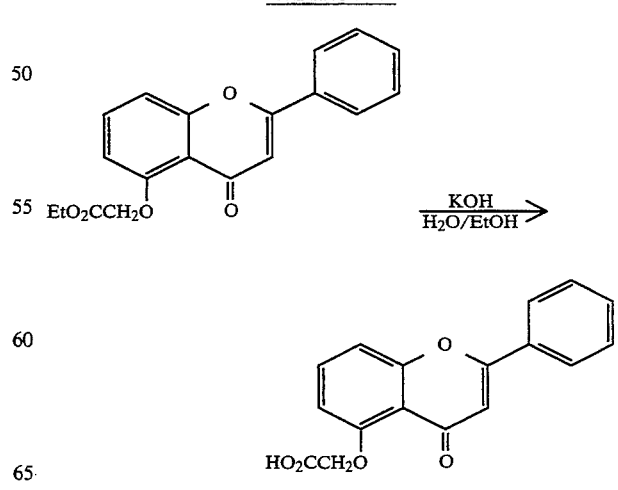

Method E is a saponification reaction which is used to prepare 5-carboxymethoxyflavone from the corresponding ethyl ester (which is itself prepared from 5-hydroxyflavone using Method D).

METHOD E

The following are non-limiting examples of synthesis methods for the subject gastroprotective agents.

Synthesis Examples

Reagents are purchased from Aldrich Chemical Company (1001 West St. Paul Ave., Milwaukee, WI, 53223, USA) unless otherwise indicated. Liquid chromatography is performed by (a) using "flash chromatography" conditions (silica gel 50×60 microns purchased from Amicon, 72 Cherry Hill Drive, Beverly, Mass. 01915), (b) filtering through a fritted-glass funnel packed with a layer of sand/flash silica gel/sand using a water aspirator vacuum (hereinafter this method is referred to as a "vacuum column"), or (c) using a Chromatotron (Harrison Research, 840 Moana Ct., Palo Alto, Calif.) on 1-, 2-, and 4-mm silica gel rotors which are prepared according to the manufacturer's instructions. Thin layer chromatography (TLC) is accomplished using silica gel GHLF (250 microns) on prescored plates (10×20 cm) obtained from Analtech Inc., 75 Blue Hen Dr., Newark, Del. 19714. Tetrahydrofuran (THF) is dried over sodium/benzophenone. Rotary evaporations are carried out using a water aspirator and 30° C. water bath. Melting points are run on a Thomas Hoover Capillary Melting Point Apparatus (Arthur H. Thomas Company, Philadelphia, Pa., USA) and are uncorrected.

METHOD A EXAMPLES

Example 1

Preparation of 2-(3-trifluoromethylphenyl)-7-methoxy-4H-1-benzopyran-4-one (1) (3'-trifluoromethyl-7-methoxyflavone): Synthesis of 1 -(2-hydroxy-4-methoxyphenyl)-3-(3-trifluoromethylphenyl)propane-1,3-dione: To a suspension of potassium-t-butoxide (1.92 g, 17.1 mmol, Spectrum Chemical Corp.) in THF (5 ml) in 0° C. bath, is added 2-hydroxy-4-methoxyacetophenone (1.30 g, 7.8 mmol) in THF (4 ml). The reaction is stirred 20 minutes at 0° C. After 20 minutes, 3(trifluoromethyl)benzoyl chloride (1.62 g, 7.8 mmol) in THF (4 ml) is added and stirred for 15 minutes at 0° C., then 10 minutes at room temperature, and finally refluxed for 3 hours. The reaction is cooled to room temperature, acidified to pH 1 with 1N HCl, and extracted with methylene chloride (3×80 ml). The combined organic layers are washed with water (1×50 ml) and dried ($Na_2SO_4$). Filtration and rotary evaporation yields the diketone which is used without purification in the next step.

Preparation of 1: A solution of the above diketone in 20 ml glacial acetic acid and 12 drops concentrated sulfuric acid is refluxed overnight. The reaction is cooled and poured into ice/water solution. This material is stirred until it becomes an unstirrable mass. The mixture is extracted with methylene chloride (3×70 ml). The combined organic layers are washed with water (1×50 ml), 5% aqueous $NaHCO_3$ solution, and dried over $Na_2SO_4$. (In some cases, the extraction step is unnecessary because the material is filterable from the aqueous layer.) Filtration and rotary evaporation gives a dark brown solid which is purified by flash chromatography (eluting with 25% ethyl acetate in hexane; material is loaded on column in methylene chloride), yielding 1 with a melting point of 142°–144° C.

Example 2

Preparation of 2-(2-chlorophenyl)-7-methoxy-4H-1-benzopyran-4-one (2) (2'-chloro-7-methoxyflavone): 2 is prepared from 2-hydroxy-4-methoxyacetophenone and 2-chlorobenzoyl chloride by the procedure of Example 1. Material is purified by flash chromatography (gradient elution using 25% ethyl acetate in hexane and 10% ethyl acetate in chloroform; material is loaded on column in methylene chloride), yielding 2 with a melting point of 148.5°–149.5° C.

Example 3

Preparation of 2-(4-trifluoromethylphenyl)-5-methoxy-4H-1-benzopyran-4-one (3) (4'-trifluoromethyl-5-methoxyflavone): 3 is prepared from 2-hydroxy-6-methoxyacetophenone and 4-trifluoromethylbenzoyl chloride by the procedure of Example 1. The material is purified by flash chromatography (gradient elution using 25% ethyl acetate in hexane, 40% ethyl acetate in hexane, 60% ethyl acetate in hexane; material is loaded on column in methylene chloride), yielding 3 with a melting point of 190°–191° C.

Example 4

Preparation of 2-phenyl-5-fluoro-4H-1-benzopyran-4-one (4) (5fluoroflavone): 4 is prepared from 2-fluoro-6-hydroxyacetophenone (see Example 6) and benzoyl chloride by the procedure of Example 1. The material is purified by flash chromatography (eluting with 25% ethyl acetate in hexane), yielding 4 with a melting point of 144°–145° C.

Example 5

Preparation of 2-fluoro-6-methoxyacetophenone (5): To a flask containing methyl magnesium bromide (1.18 g, 9.93 mmol) in ether is added dropwise 2-fluoro-6-methoxybenzonitrile (0.5 g, 3.31 mmol, Lancaster Synthesis Inc.) in benzene (9 ml). The reaction mixture is refluxed overnight. The reaction is cooled to room temperature and quenched slowly with saturated ammonium chloride (15 ml) and concentrated hydrochloric acid (1 ml). The mixture is extracted with diethyl ether (2×50 ml). The combined organic layers are dried over $Na_2SO_4$, filtered, and rotary evaporated to give 0.55 g of a crude yellow material. Purification is accomplished by vacuum column (eluting with 16% ethyl acetate in hexane). The compoundcontaining fractions are combined, yielding 5.

Example 6

Preparation of 2-fluoro-6-hydroxyacetophenone(6): To a solution of 5 (0.48 g, 2.85 mmol) in methylene chloride (15 ml), cooled to 0° C. is added boron tribromide (1.43 g, 5.71 mmol) in methylene chloride. The reaction is stirred overnight at room temperature. The green-orange solution is poured in ice/water and stirred. The mixture is extracted with methylene chloride (3×80 ml). The combined organic layers are dried over $Na_2SO_4$, filtered, and rotary evaporated to give 0.37 g crude product. This material is purified by vacuum column (eluting with 10% ethyl acetate in hexane ), yielding 6.

Example 7

Preparation of 2-(2-methylphenyl)-4H-1-benzopyran-4-one (7) (2'-methylflavone): 7 is prepared from 2-methylbenzoyl chloride (8) and 2-hydroxyacetophenone by the procedure of Example 1. The material is purified by vacuum column (eluting with 10% ethyl acetate in hexane), yielding 7 with a melting point of 45.5°–47.5° C.

Example 8

Preparation of 2-methylbenzoyl chloride (8): To a suspension of o-toluic acid (1.0 g, 7.35 mmol) in methylene chloride (15 ml) is added oxalyl chloride (1.17 g, 9.19 mmol) and dimethyl formamide (DMF) (0.05 g, 0.74 mmol, previously dried over 4A sieves). The reaction is stirred at room temperature 3.5 hrs. The methylene chloride is rotary evaporated and the residue is treated with methylene chloride (2×20 ml) and reevaporated to yield the acid chloride, which is used without purification in the next step.

Example 9

Preparation of 2-(2-fluorophenyl)-4H-1-benzopyran-4-one (9) (2'-fluoroflavone): 9 is prepared from 2-fluorobenzoic acid and 2-hydroxyacetophenone by the procedures of Examples 7 and 8. The crude material is purified by vacuum column (gradient elution using 10% ethyl acetate in hexane, 20% ethyl acetate in hexane, and 30% ethyl acetate in hexane). The material is then recrystallized from hexane/ethyl acetate, yielding 9 with a melting point of 98°–100° C.

Example 10

Preparation of 2-(4-fluorophenyl)-7-methoxy-4H-1-benzopyran-4-one (10) (4'-fluoro-7-methoxyflavone): 10 is prepared from 4-fluorobenzoic acid and 2-hydroxy-4-methoxyacetophenone by the procedures of Examples 7 and 8. The crude material is partially purified by flash chromatography (gradient elution using 25% ethyl acetate in hexane, 40% ethyl acetate in hexane, and 70% ethyl acetate in hexane; the material is loaded on the column in methylene chloride). The material is recrystallized from ethyl acetate/hexane, yielding 10 with a melting point of 161.5°–162.5° C.

METHOD B EXAMPLES

Example 11

Preparation of 2-( 3, 5-difluorophenyl )-5-methoxy -4H- 1 -benzopyran-4-one (11) (3', 5'-difluoro-5-methoxyflavone):

Synthesis of 1-(2-hydroxy-6-methoxyphenyl)-3-(3,5-difluoro phenyl)propane-1,3-dione: To a suspension of potassium t-butoxide (1.35 g, 12.08 mmol) and THF (6 ml) at 0° C. is added 2-hydroxy-6-methoxyacetophenone (1.8 g, 11 mmol) in THF (7 ml). The reaction is stirred for 0.5 hour at room temperature. The green solution is cooled to 0° C. and 3,5-difluorobenzoyl chloride (1.98 g, 11.25 mmol) is added. The reaction is stirred at room temperature 1 hour, cooled to 0° C., and potassium t-butoxide (1.35 g, 12.08 mmol) is added. The reaction is heated at reflux overnight. Upon reaction completion, a 50/50 mixture of concentrated HCl/water is added until the pH of the reaction mixture reaches 2. This aqueous material is extracted with methylene chloride (3×80 ml). The combined organic layers are washed with water (2×50 ml), dried over Na2SO4, filtered, and rotary evaporated to yield the diketone which is used without purification in the next step.

Preparation of 11: The above diketone is cyclized as described in Example 1 and purified by recrystallization from isopropanol and further purified by vacuum column (eluting with 100% methylene chloride), yielding 11 with a melting point of 206°–207° C.

Example 12

Preparation of 2-(3,5-ditrifluoromethylphenyl)-5-methoxy-4H-1-benzopyran-4-one (12) (3',5'-ditrifluoromethyl-5-methoxyflavone): 12 is prepared from 2-hydroxy-6-methoxyacetophenone and 3,5-bis (trifluoromethyl)benzoyl chloride by the procedure of Example 11. The crude material is purified by vacuum column (eluting with 100% methylene chloride). This material is recrystallized from isopropanol two times, but still has a small impurity by TLC. The material is then further purified by vacuum column (eluting with 100% methylene chloride), yielding 12 with a melting point of 212°–213° C.

Example 13

Preparation of 2-(2-chlorophenyl)-5-methoxy-4H-1-benzopyran-4-one (13) (2'-chloro-5-methoxyflavone): 13 is prepared from 2-hydroxy-6-methoxyacetophenone and 2-chlorobenzoyl chloride by the procedure of Example 11. The material is purified by recrystallization from isopropanol, yielding 13 with a melting point of 148°–149° C.

Example 14

Preparation of 2-(4-fluorophenyl)-5-methoxy-4H-1-benzopyran-4-one (14) (4'-fluoro-5-methoxyflavone): 14 is prepared from 2-hydroxy-6methoxyacetophenone and 4-fluorobenzoyl chloride by the procedure of Example 11. The material is purified by recrystallization from isopropanol, yielding 14 with a melting point of 177.5°–178.5° C.

Example 15

Preparation of 2-(3-(trifluoromethylphenyl))-5-methoxy-4H-1-benzopyran-4-one (15) (3'-trifluoromethyl-5-methoxyflavone): 15 is prepared from 2-hydroxy-6-methoxyacetophenone and 3-trifluoromethylbenzoyl chloride by the procedure of Example 11. The material is purified by recrystallization from ethanol, yielding 15 with a melting point of 184°–185° C.

Example 16

Preparation of 2-(4-methylphenyl)-5-methoxy-4H-1-benzopyran-4-one (16) (4'-methyl-5-methoxyflavone): 16 is prepared from 2-hydroxy-6methoxyacetophenone and p-toluoyl chloride by the procedure of Example 11. The material is purified by flash chromatography using methylene chloride/methanol, yielding 16 with a melting point of 169°–171 ° C.

Example 17

Preparation of 2-(4-chlorophenyl)-5-methoxy-4H-1-benzopyran-4-one (17) (4'-chloro-5-methoxyflavone): 17 is prepared from 2-hydroxy-6methoxyacetophenone and 4-chlorobenzoyl chloride by the procedure of Example 11. The material is purified by recrystallization from isopropanol, yielding 17 with a melting point of 171°–172° C.

METHOD C EXAMPLES

Examples 18 and 19

Preparation of 2-phenyl-5-methyl-4H-1-benzopyran-4-one (18) (5methylflavone) and 2-phenyl-7-methyl-4H-1-benzopyran-4-one (19) (7methylflavone): 18 and 19 are prepared from m-cresol and ethyl phenylpropiolate by the procedure disclosed in Ruhemann, S., "Uberein einfaches Verfahren zur Darstellung der Flavone und uber die Synthese des Thioflavons", *Berichte*, Vol. 46 (1913), pp. 2188-2197, which yields two isomers. These am purified by Chromatotron (eluting with 15% ethyl acetate in hexane), yielding 18 with a melting point of 125°-127° C. and 19 with a melting point of 120°-121° C.

METHOD D EXAMPLES

Example 20

Preparation of 2-phenyl-5-ethoxycarbonylmethoxy-4H-1-benzopyran-4-one (20) (5-ethoxycarbonylmethoxyflavone): A mixture of 5-hydroxyflavone (0.5 g, 2.1 mmol, Indofine Chemical Company Inc.), potassium carbonate (2.9 g, 21.0 mmol, Fisher Scientific), ethyl chloroacetate (1.28 g, 10.5 mmol) and acetone (20 ml) are refluxed 72 hours. Upon completion, the reaction is filtered and the cake of $K_2CO_4$ is washed well with acetone. The solution is rotary evaporated, and the resulting product is purified by vacuum column (eluting with 50% ethyl acetate in hexane). The material is repurified by flash column chromatography (50% ethyl acetate in hexane), yielding 20 with a melting point of 89.5°-90.5° C.

Example 21

Preparation of 2-phenyl-7-ethoxy-4H-1-benzopyran-4-one (21) (7ethoxyflavone): 21 is prepared from 5-hydroxyflavone (Indofine) and iodoethane by the procedure of Example 20. The material is recrystallized from isopropanol, yielding 21 with a melting point of 138°-139° C.

Example 22

Preparation of 2-phenyl-5-ethoxy-4H-1-benzopyran-4-one (22) (5ethoxyflavone): 22 is prepared from 5-hydroxyflavone (Indofine) and iodoethane by the procedure of Example 20. The material is purified by flash column chromatography (gradient elution of 60% ethyl acetate in hexane, 80% ethyl acetate in hexane, and 100% ethyl acetate), yielding 22 with a melting point of 111°-113° C.

Example 23

Preparation of 2-phenyl-5-butoxy-4H-1-benzopyran-4-one (23) (5butoxyflavone): 23 is prepared from 5-hydroxyflavone (Indofine) and 1-iodobutane by the procedure of Example 20. The material is purified by vacuum column (eluting with 25% ethyl acetate in hexane), flash column chromatography (20% ethyl acetate in hexane), and then recrystallized from ethyl acetate, yielding 23 with a melting point of 96°-97° C.

Example 24

Preparation of 2-phenyl-5-(1-methylethoxy)-4H-1-benzopyran-4-one (24) (5-isopropoxyflavone): 24 is prepared from 5-hydroxy flavone (Indofine) and 2-iodopropane first by the procedure of Example 20, and then repeated, using potassium hydroxide in place of potassium carbonate. The crude materials are combined from the two reactions and purified by flash column chromatography (eluting with 25% ethyl acetate in hexane) and by vacuum column (eluting with 25% ethyl acetate in hexane), yielding 24 with a melting point of 98°-99° C.

METHOD E EXAMPLE

Example 25

Preparation of 2-phenyl-5-carboxymethoxy-4H-1-benzopyran-4-one (25) (5-carboxymethoxyflavone): To a solution of 20 (0.72 g, 2.22 mmol) in 10 ml of ethanol, is added 10% aqueous KOH solution (10 ml). The reaction is stirred at room temperature for 72 hours. The reaction is acidified with 6N HCl and a precipitate forms. The mixture is rotary evaporated to remove the ethanol. The precipitate is filtered and washed with water. The crude material is recrystallized from acetic acid to yield yellow crystals of 25 with a melting point of >200° C.

While particular embodiments of the subject invention have been described, it will be obvious to those skilled in the art that various changes and modifications to the subject invention can be made without departing from the spirit and scope of the invention. It is intended to cover, in the appended claims, all such modifications that are within the scope of the subject invention.

What is claimed is:

1. A composition useful for prevention or treatment of damage to the mucosal lining of the gastrointestinal tract of a human or lower animal comprising:

1) a safe and effective amount of a compound having the structure:

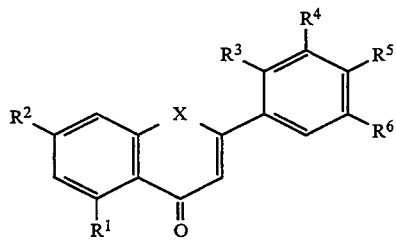

wherein
   a) X is independently O or S;
   b) $R^1$ is selected from the group consisting of hydrogen, fluoro, methoxy and carboxymethoxy and its methyl and ethyl esters; $R^2$ is selected from the group consisting of hydrogen, methoxy, ethoxy, methyl, carboxymethoxy and its methyl and ethyl esters; and furthermore either, but not both, $R^1$ or $R^2$ is hydrogen or both $R^1$ and $R^2$ are methoxy;
   c) $R^3$ is selected from the group consisting of hydrogen, hydroxy, methoxy, methyl, chloro and fluoro; and
   d) $R^4$, $R^5$ and $R^6$ are all hydrogen; or if one of $R^1$ and $R^2$ is other than hydrogen; $R^4$ is selected from the group consisting of hydrogen, fluoro, chloro and trifluoromethyl; $R^5$ is hydrogen; $R^6$ is selected from the group consisting of hydrogen, fluoro and chloro; and
   e) no more than two of $R^3$, $R^4$, $R^5$ and $R^6$ are other than hydrogen; and 2) a pharmaceutically-acceptable carrier.

2. The composition of claim 1 wherein no more than one of $R^3$, $R^4$, and $R^6$ is other than hydrogen.

3. The composition of claim 2 wherein X is oxygen.

4. The composition of claim 2 wherein $R^1$ is methoxy, $R^2$ is hydrogen or methoxy, and $R^4$ and $R^6$ are hydrogen.

5. A composition useful for prevention or treatment of damage to the mucosal lining of the gastrointestinal tract of a human or lower animal comprising: (1) a safe and effective amount of a compound selected from the group consisting of 1-thioflavone, 5-methoxyflavone, 5-fluoroflavone, 7-methoxyflavone, 7-methylflavone, 7-ethoxyflavone, 2'-hydroxyflavone, 2'-methoxyflavone, 2'-methylflavone, 2'-fluoroflavone, 4'-fluoro-5-methoxyflavone, 3'-trifluoromethyl-5-methoxyflavone, 2'-chloro-5-methoxyflavone, 4'-methyl-5-methoxyflavone, 4'-chloro-5-methoxyflavone, 5,7-dimethoxyflavone, 5-carboxymethoxyflavone, 7-carboxymethoxyflavone, 5-ethoxycarbonylmethoxyflavone, 7-ethoxycarbonylmethoxyflavone, and 2'-chloro-7-methoxyflavone; and (2) a pharmaceutically-acceptable carrier.

6. The composition of claim 5 wherein the compound is selected from the group consisting of 1-thioflavone, 5,7-dimethoxyflavone, 4'-fluoro-5-methoxyflavone, 4'-chloro-5-methoxyflavone, and 2-fluoroflavone.

7. The composition of claim 1, 2 or 5 wherein the compound is in a solid, particulate form with 95% of the compound particles having a particle size of less than about 100 microns.

8. The composition of claim 1, 2, or 5 wherein the compound is in a solid, particulate form with 95% of the compound particles having a particle size of less than about 10 microns.

9. The composition of claim 6 wherein the composition additionally comprises an effective amount of a NSAID.

10. The composition of claim 6 wherein the composition additionally comprises an effective amount of naproxyn.

11. The composition of claim 6 wherein the composition additionally comprises an effective amount of ketorolac.

12. A method for preventing or treating damage to the mucosal lining of the gastrointestinal tract of a human or lower animal in need thereof comprising administration of a safe and effective amount of a compound having the structure:

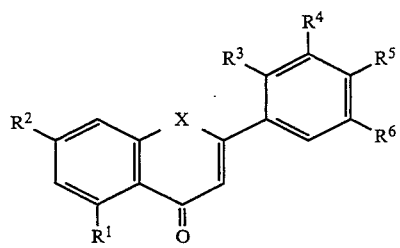

wherein
a) X is independently O or S;
b) $R^1$ is selected from the group consisting of hydrogen, fluoro, methoxy and carboxymethoxy and its methyl and ethyl esters; $R^2$ is selected from the group consisting of hydrogen, methoxy, ethoxy, methyl, carboxymethoxy and its methyl and ethyl esters; and furthermore either $R^1$ or $R^2$ is hydrogen or both $R^1$ and $R^2$ are methoxy;
c) $R^3$ is selected from the group consisting of hydrogen, hydroxy, methoxy, methyl, chloro and fluoro; and
d) $R^4$, $R^5$ and $R^6$ are all hydrogen; or if one of $R^1$ and $R^2$ is other than hydrogen; $R^4$ is selected from the group consisting of hydrogen, fluoro, chloro and trifluoromethyl; $R^5$ is selected from the group consisting of hydrogen, methyl, fluoro and chloro; $R^6$ is selected from the group consisting of hydrogen, fluoro and chloro; and
e) no more than two of $R^3$, $R^4$, $R^5$ and $R^6$ are other than hydrogen.

13. The method of claim 12 wherein no more than one of $R^3$, $R^4$, $R^5$, and $R^6$ is other than hydrogen.

14. The method of claim 13 wherein X is oxygen.

15. The method of claim 13 wherein $R^1$ is methoxy, $R^2$ is hydrogen or methoxy, and $R^4$ and $R^6$ are hydrogen.

16. The method of claim 12 wherein the compound is selected from the group consisting of flavone, 1-thioflavone, 5-methoxyflavone, 5-fluoroflavone, 7-methoxyflavone, 7-methylflavone, 7-ethoxyflavone, 2'-hydroxyflavone, 2'-methoxyflavone, 2'-methylflavone, 2'-fluoroflavone, 4'-fluoro-5-methoxyflavone, 3'-trifluoromethyl-5-methoxyflavone, 2'-chloro-5-methoxyflavone, 4'-methyl-5-methoxyflavone, 4'-chloro-5-methoxyflavone, 5,7-dimethoxyflavone, 5-carboxymethoxyflavone, 7-carboxymethoxyflavone, 5-ethoxycarbonylmethoxyflavone, 7-ethoxycarbonylmethoxyflavone, and 2'-chloro-7-methoxyflavone.

17. The method of claim 12 wherein the compound is selected from the group consisting of 1-thioflavone, 5,7-dimethoxyflavone, 4'-fluoro-5-methoxyflavone, 4'-chloro-5-methoxyflavone, and 2-fluoroflavone.

18. The method of claim 17 wherein the damage prevented or treated is NSAID-induced damage.

19. The method of claim 12, 14 or 16 wherein damage to the mucosal lining of the stomach is prevented.

* * * * *